United States Patent [19]

Torrence

[11] Patent Number: 4,733,668

[45] Date of Patent: Mar. 29, 1988

[54] METHOD AND APPARATUS FOR COMPENSATION DURING ULTRASOUND EXAMINATION

[75] Inventor: Kenneth R. Torrence, Huntington Beach, Calif.

[73] Assignee: North American Philips Corporation, New York, N.Y.

[21] Appl. No.: 72,717

[22] Filed: Sep. 4, 1979

[51] Int. Cl.$^4$ .............................................. A61B 10/00
[52] U.S. Cl. ........................................ 128/660; 73/631
[58] Field of Search .............................. 128/660–661; 73/609–612, 631

[56] References Cited

U.S. PATENT DOCUMENTS

| 3,690,153 | 9/1972 | Matay | 73/631 |
| 4,008,713 | 2/1977 | Griffith et al. | 73/631 |
| 4,016,750 | 4/1977 | Green | 73/631 |
| 4,043,181 | 8/1977 | Nigam | 73/631 |
| 4,057,049 | 11/1977 | Hill | 128/660 |
| 4,140,107 | 2/1979 | Lancee et al. | 128/660 |
| 4,145,741 | 3/1979 | Nappin | 73/631 |

OTHER PUBLICATIONS

Susal, A. L., "An Opthalmic Ultrasound Scanning System", Ultrasonics, Jan. 1974.

Primary Examiner—Francis J. Jaworski
Attorney, Agent, or Firm—Jack E. Haken

[57] ABSTRACT

The time-gain function of an ultrasound receiver for medical examinations is modified to compensate for different attenuation characteristics in body structures. The slope of the time-gain function is increased at times associated with pulse transmission through the highly attenuating body wall and may be decreased at times associated with pulse transmission through fluid filled body structures. The time-gain compensation, in combination with probe focus compensation and a highly linear receiver transfer function provides sharply increased diagnostic quality. The location and attenuating characteristics of body structures may be determined from a prior knowledge of their depth within the body or from distinctive signatures in ultrasound echos.

11 Claims, 10 Drawing Figures

1

METHOD AND APPARATUS FOR COMPENSATION DURING ULTRASOUND EXAMINATION

BACKGROUND OF THE INVENTION

The invention relates to methods and apparatus for medical examination by means of ultrasound echos. More specifically, the invention relates to methods and apparatus for compensating the characteristics of ultrasound receivers to eliminate distortion which may be introduced by variations in attenuating characteristics of body structures.

Ultrasound pulse echo techniques have been utilized in the prior art to locate, image, determine the motion of, and otherwise characterize internal structures of the human body. In such systems, a pulse of ultrasonic energy is caused to propagate into the body, where it may be reflected by discontinuities along its propagation path (such discontinuities may, for example, occur at the boundaries of body organs) The time and magnitude of the reflected echos are measured and utilized, for example, to produce cross-section images (B-scans) of internal body structures. The techniques utilized in medical ultrasound systems are similar to those used in sonar systems, however special problems result from the significantly smaller size of the structures to be examined and from the unusual attenuating characteristics of body tissues.

It is known, from the prior art, that body tissues on the average attenuate ultrasound energy at a rate of approximately 1 dB./mHz/cm. To compensate for this rapid attenuation, prior art ultrasound systems generally incorporate circuitry (termed "time-gain compensation" or TGC circuitry) which acts to increase receiver gain during a time period which follows the introduction of a pulse into the body. The time required for reflected pulses to return to the receiver is a direct function of the depth of a reflecting structure within the body; thus receiver gain is automatically increased for reflected pulses which originate deep within the body. The attenuation of ultrasound energy is, however, not uniform for all body tissues and structures. The body wall is substantially more attenuating than average body tissues while fluid filled structures, for example cysts, are substantially less attenuating than average body tissues. The term "cyst", as used herein and in the claims which follow, refers to any fluid filled cavity within the body and includes, for example, the urinary bladder and, in some cases, larger blood vessels.

SUMMARY OF THE INVENTION

In accordance with the invention the slope of the time-gain compensation applied to the receiver of an echo ultrasound system is caused to vary as a function of the attenuation characteristic for ultrasound energy in tissues at a corresponding depth in a body being examined. The depth of structures having a particular attenuation characteristic may be known a priori (as for example in the case of the body wall) in which case changes in the slope of the time-gain compensation may be caused to occur at predetermined fixed times. Alternately, the depth of such structures may be determined from characteristic signature information in ultrasound echos. For example, the attenuation characteristics of body tissues may be related to the amount of scattered ultrasound energy returned from those tissues. A high level of returned scattered energy is characteristic of highly attenuating body wall structures while a very low level of returned scattered energy is characteristic of pulse transmission through a fluid. Scattered energy may be detected and applied to thresholding circuits which increase the slope of the time-gain compensation in the case of high levels of scattered energy (which indicate transmission through the body wall) or which may reduce the slope of the time-gain compensation to zero or a near zero level in the case of a weakly attenuating cyst.

Most ultrasound transducers used in echo ultrasound systems are focused (for example, at a distance of several centimeters) and are thus characterized by a sensitivity to reflected energy which varies as a function of the depth of a reflecting structure within a body. Accurate compensation for the varying attenuation of body structures and tissues can be accomplished if the time-gain characteristic of the amplifier is further compensated to cancel the focusing effects of the ultrasonic transducer. Likewise, it has been found that the techniques for compensating for body wall attenuation of the present invention are only effective for improving diagnostic image quality if the TGC-gain transfer characteristics of the ultrasound receiver are maintained substantially more linear than those of the prior art.

BRIEF DESCRIPTION OF THE DRAWINGS

The invention is described with reference to the attached drawings in which.

DESCRIPTION OF THE PREFERRED EMBODIMENTS

Figure 1:
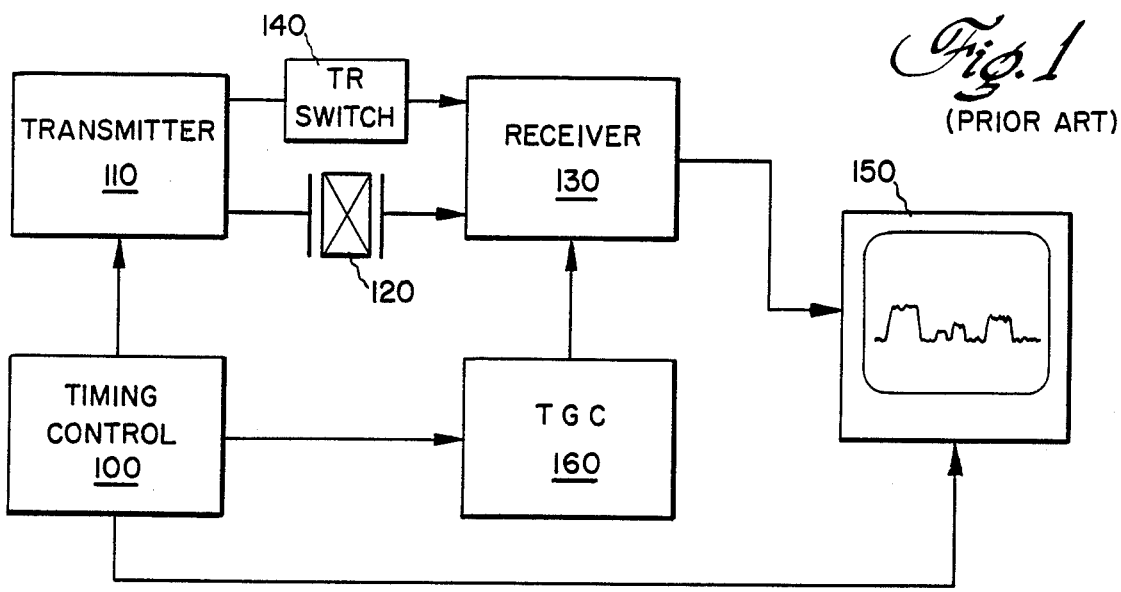
FIG. 1 illustrates a typical echo ultrasound system of the prior art.

FIG. 1 is an echo ultrasound system of the prior art. A timing control circuit 100 provides a signal to an ultrasound pulse transmitter 110 which causes the transmitter to drive a transducer 120 with an electrical current pulse. In response to the current pulse the transducer projects a pulse of ultrasound energy (typically at a frequency of approximately 3.5 mHz) into the body of a patient. The ultrasound energy transmitted into the patient is reflected from interfaces or discontinuities in the body and the echos thus produced are received by the transducer 120 and applied to the input of a gain controlled receiver 130. A T-R switch 140 disables the input of the receiver during transmission to prevent overloads.

The timing control 100 also initiates an appropriate sweep on a display 150 (which may be a CRT). The echos received by the transducer are amplified in the receiver 130 and are likewise applied to the display 150. A number of alternate display modes are commonly utilized for the display of medical ultrasound information. For example, in what is commonly termed the A-mode, displacement along the horizontal axis of the display represents the time of reception of echos (which corresponds to the depth of the echo producing structure) while the amplitude of received pulses is displayed along the vertical axis. In other display modes the output signal from the receiver may be utilized to modulate the intensity at points on a displayed image which correspond to positions in a plane intersecting the body.

Figure 2:
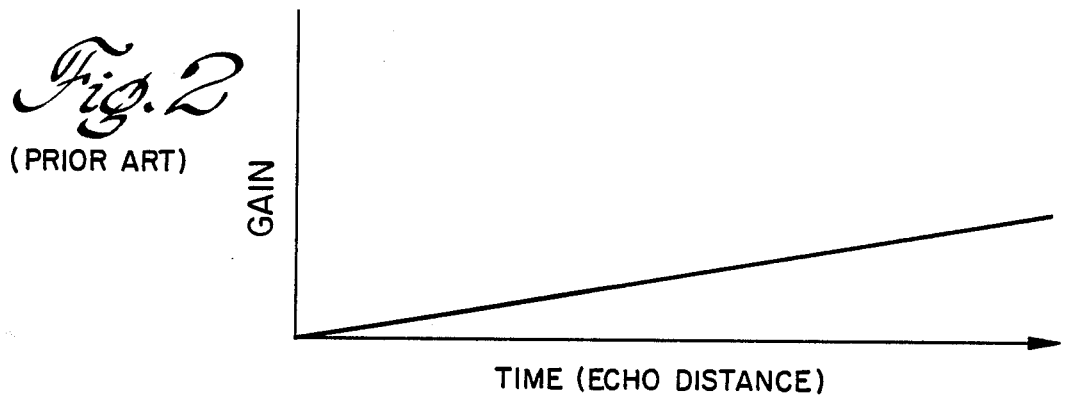
FIG. 2 is a typical time-gain compensation curve of the prior art.

Typically, the gain of the receiver 130 is controlled by an electrical signal which is furnished by a time-gain control (TGC) circuit 160 to compensate for the attenuation of ultrasound energy which is reflected from structures at varying depths in the body. Ultrasound waves travel through body tissue at a nominal velocity of 1540 m/sec. Thus, it takes 6.5 microseconds for the transmitted pulse to penetrate 1 cm. into the body and a returning echo from an interface 1 cm. deep will reach the receiver 13 microseconds after the pulse is transmitted (each additional centimeter depth will delay the signal by another 13 microseconds). By equating tissue depth with the lapse time after the transmitted pulse, the receiver gain is controlled to attenuate very strong echos which are produced near the transducer while allowing progressively greater gain for echos from deeper interfaces. In the prior art, the timing control circuit 100 caused the time-gain compensation circuit 160 to generate a linear ramp (FIG. 2) which cause the gain of the receiver 130 to increase by approximately 1 dB/cm/mHz which corresponds to an increase in gain of 1/13 dB/microsec/mHz.

Figure 3:
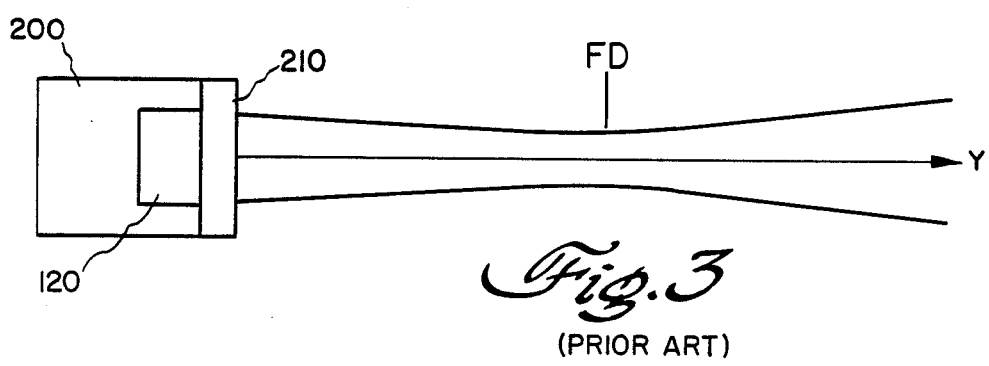
FIG. 3 illustrates an ultrasound transducer having a focused characteristic.

FIG. 3 schematically illustrates a prior art ultrasound probe 200 which contains the transducer 120. Ultrasound energy projected from the face 210 of the probe typically forms a beam which converges to a focus at a short distance FD (for example 9 cm) from the probe face. Ultrasound energy from the probe is thus concentrated over a smaller area at a distance FD from the probe than it is at distances which are closer to or further from the probe. The probe is thus be more sensitive to echos which originate at the distance FD than it is to echos which originate from interfaces which are closer to the probe or further from the probe than the FD. The gain of the receiver may be adjusted to compensate for the focusing effects of the ultrasound probe by superimposing a dual ramp probe compensation signal (FIG. 6) on the time-gain compensation. Typically the slope of the probe compensation signal is much smaller than that of the time-gain compensation signal. The probe compensation signal functions to decrease the gain of the receiver at times corresponding to echos which originate at the focal distance of the probe and to increase the gain of the receiver for echos which originate from other distances.

Figure 4:
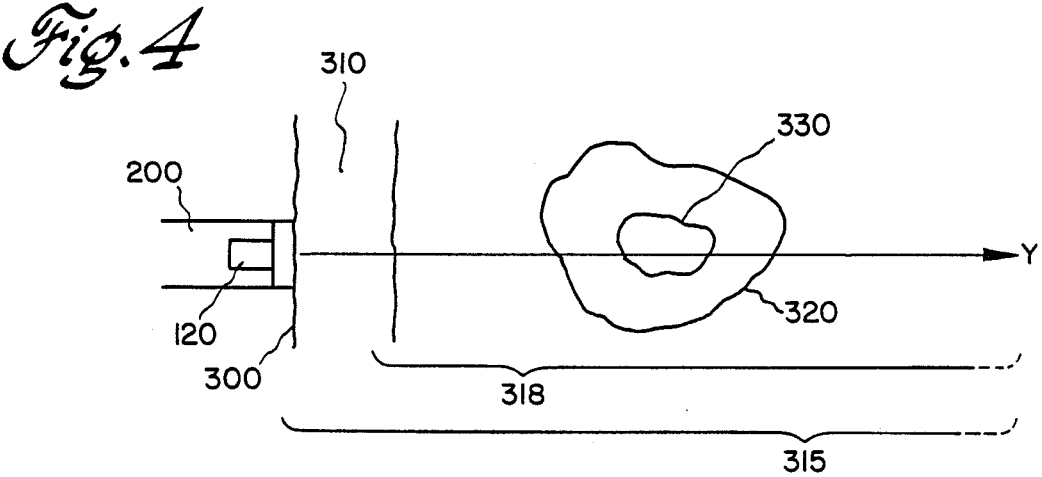
FIG. 4 illustrates the transmission of an ultrasound pulse through the body.

FIG. 4 illustrates a typical application of an echo ultrasound system. The probe 200 is placed against the skin 300 of a patient and projects pulses of ultrasound energy along an axis Y into the body 315. The ultrasound pulse must first penetrate the skin 300 and muscle layers of the body wall 310. It then propagates through the internal structures of the body 318. Interfaces between various body structures present discontinuities which reflect echos of the pulse back to the probe 200. The interfaces may represent the boundaries of body organs 320. The pulse may also propagate through a cyst 330. As the pulse propagates through the structures it is attenuated at a nominal rate of approximately 1 dB/cm/mHz.

Figure 5:
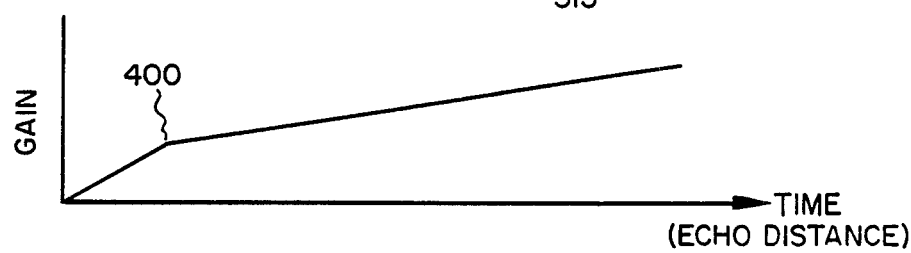
FIG. 5 is a time-gain compensation curve of the present invention.

The attenuation of specific body structures is known to differ from the nominal attenuation stated above. Thus, the body wall 310 is known to attenuate ultrasound energy at a substantially greater rate than the nominal value while cysts are known to attenuate ultrasound energy at a substantially lower rate than the nominal value. In accordance with the invention, the slope of the time-gain compensation applied to the receiver in a diagnostic ultrasound system is caused to vary with time to match the attenuation characteristic of tissue at depths corresponding to those times. FIG. 5 represents a time-gain compensation curve which compensates for the high attenuation which is known to exist in the body wall. The slope of the time-gain compensation curve is higher during the first approximately 13 microseconds following pulse transmission and is smaller after that time. The break point 400 in the time-gain compensation curve, may, in the case of body wall compensation, be set to occur at a fixed time (following transmission of the pulse) which corresponds to the approximate thickness of the body wall. This time may be set at a nominal value determined from previous experience or may be set by reference to the echo which occurs at the interface between the body wall and the internal body tissues.

Figure 6:
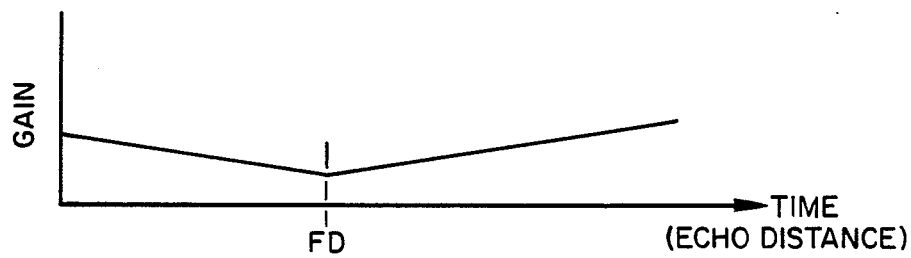
FIG. 6 illustrates a probe compensation curve utilized in the present invention.

In order to produce effective improvements in the diagnostic quality of echo ultrasound images, the dual-slope time-gain compensation of FIG. 5 must be combined with probe focal depth compensation (illustrated in FIG. 6). In addition, it has been found that useful improvements in the diagnostic quality of the ultrasound display are only obtainable if the transfer function of the ultrasound receiver is substantially more linear than prior art receivers. Prior art ultrasound receivers had transfer functions which, at best, were linear to within plus or minus 3 dB. The methods of the present invention are, however, only useful to improve diagnostic image quality if the linearity of the transfer function of the ultrasound receiver is maintained within plus or minus 1 dB. In this specification and in the claims which follow linearity of transfer functions is specified over the entire dynamic working range of a receiver.

Figure 7:
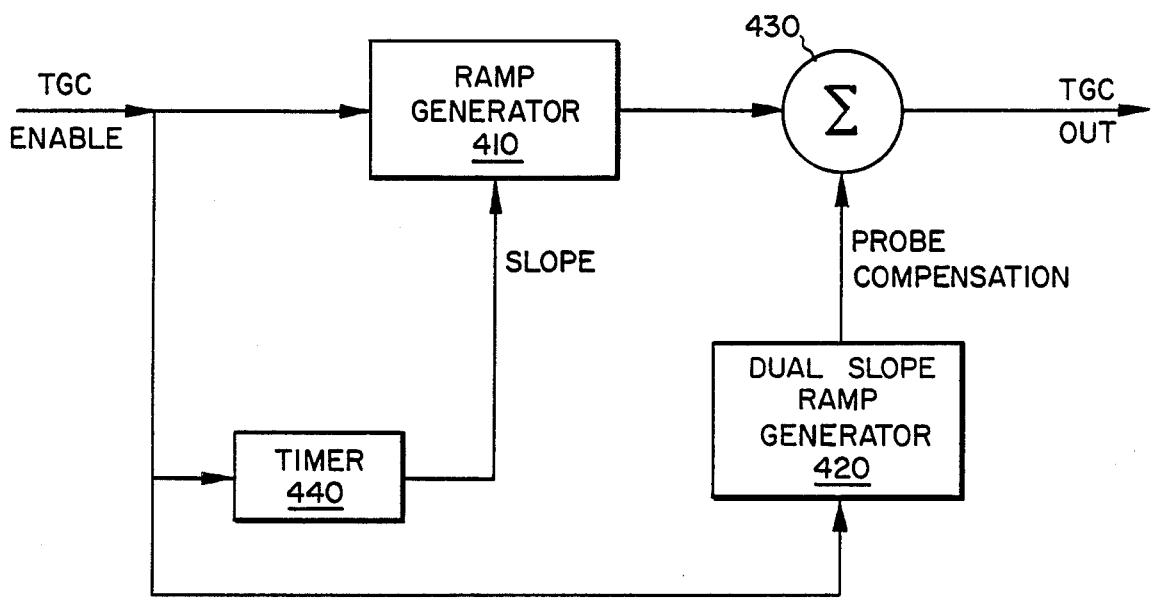
FIG. 7 is a compensation circuit of the present invention which utilizes a priori knowledge of the location of body structures.

FIG. 7 illustrates a circuit for producing the time-gain compensation signal of the present invention. A TGC Enable signal is received from the timing control circuit 100 (FIG. 1). The TGC Enable signal triggers a ramp generator, 410 which may be an integrator, to produce a linear ramp time-gain compensation signal in the manner of the prior art. The TGC Enable signal also triggers a dual slope ramp generator 420 which produces a probe compensation signal. The output of the ramp generator 410 and the dual slope ramp generator 420 are added in a summer 430 to produce a time-gain compensation output signal which is applied to the receiver 130 (FIG. 1). The TGC enable signal also triggers a timer 440. After a time interval which corresponds to the thickness of the body wall the timer applies a signal to the ramp generator 410 which reduces the slope of its ramp output. Typically, the timer output signal may actuate a switch in the ramp generator which adds capacitance or resistance to an RC integrator circuit.

Figure 8:
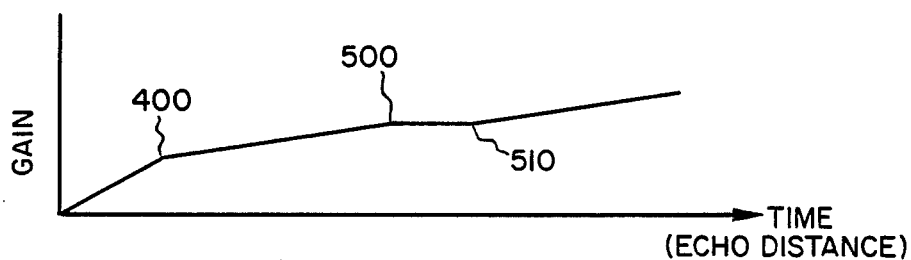
FIG. 8 is a time-gain compensation curve of the present invention.

FIG. 8 illustrates a time-gain compensation curve which is further adapted to compensate for the lower attenuation of ultrasound energy which occurs in cysts or fluid filled cavities. As in FIG. 5, the slope of the time-gain compensation is maintained at a high level at times which correspond to echos from the body wall and is reduced to a lower level following a break point 400. The slope of the time-gain compensation for the curve is further reduced to zero or approximately zero, at times which correspond to the transmission of ultrasound energy through the boundary of a cyst 330 (at break point 500) and is increased (at break point 510) to its previous value at a time which corresponds to the depth of the most distant boundary of the cyst.

Figure 9:
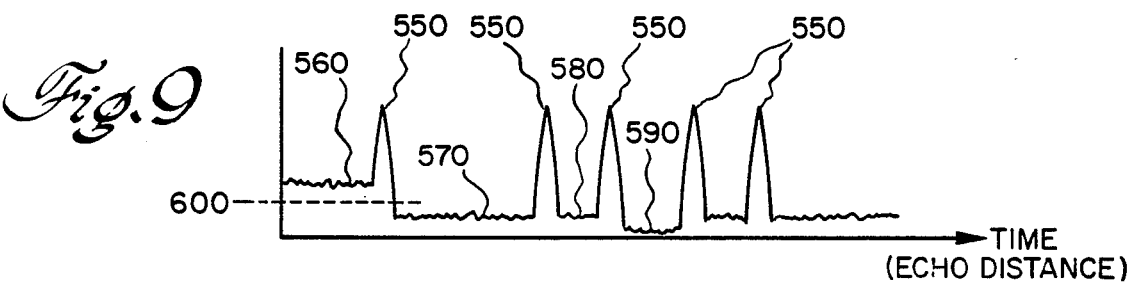
FIG. 9 is the output of an ultrasound receiver produced by the configuration of FIG. 4.

The depth of a cyst or fluid filled cavity within the body may be determined by an experienced operator from examination of an uncompensated ultrasound display. It is possible, however, to determine the depth of attenuating structures within the body from information contained in characteristic signatures which are present in returned echos. FIG. 9 illustrates a typical train of echos which are returned to the probe 200 by the body structures of FIG. 4 and which is subjected to TGC compensation for example by the methods of the prior art. The train is characterised by distinct, higher level echos 550 which are returned from interfaces in the body structure and by regions containing lower level signals 560, 570, 580 which are produced by scatter of ultrasound energy in the tissue. There is virtually no scatter in the fluid filled cyst 330 which corresponds to region 590 of the echo train. The dense body wall 310 produces a substantially higher level of scatter returns in the region 560 than the internal body structures do in the regions 570 and 580.

The level of scatter echo returns may, thus, be associated with the type or attenuation of tissue regions and utilized to adjust the slope of the TGC curve to compensate for varying tissue attenuation. A first threshold level 600 is selected (between the scatter echo level characteristic of the body wall in the region 560 and the scatter echo level characteristic of internal body tissues in the region 570). The break point 400 in the TGC curve (FIG. 9) is determined when the scatter echo level first falls below the threshold 600. Likewise a second threshold may be determined between the scatter echo level characteristic of internal body tissues (for example in the region 580) and that characteristic of fluid filled cysts (for example in the region 590). The slope of the TGC curve is then reduced to virtually zero whenever the scatter echo return level falls below the second threshold and is increased to its previous value whenever the scatter echo return exceeds that threshold.

Figure 10:
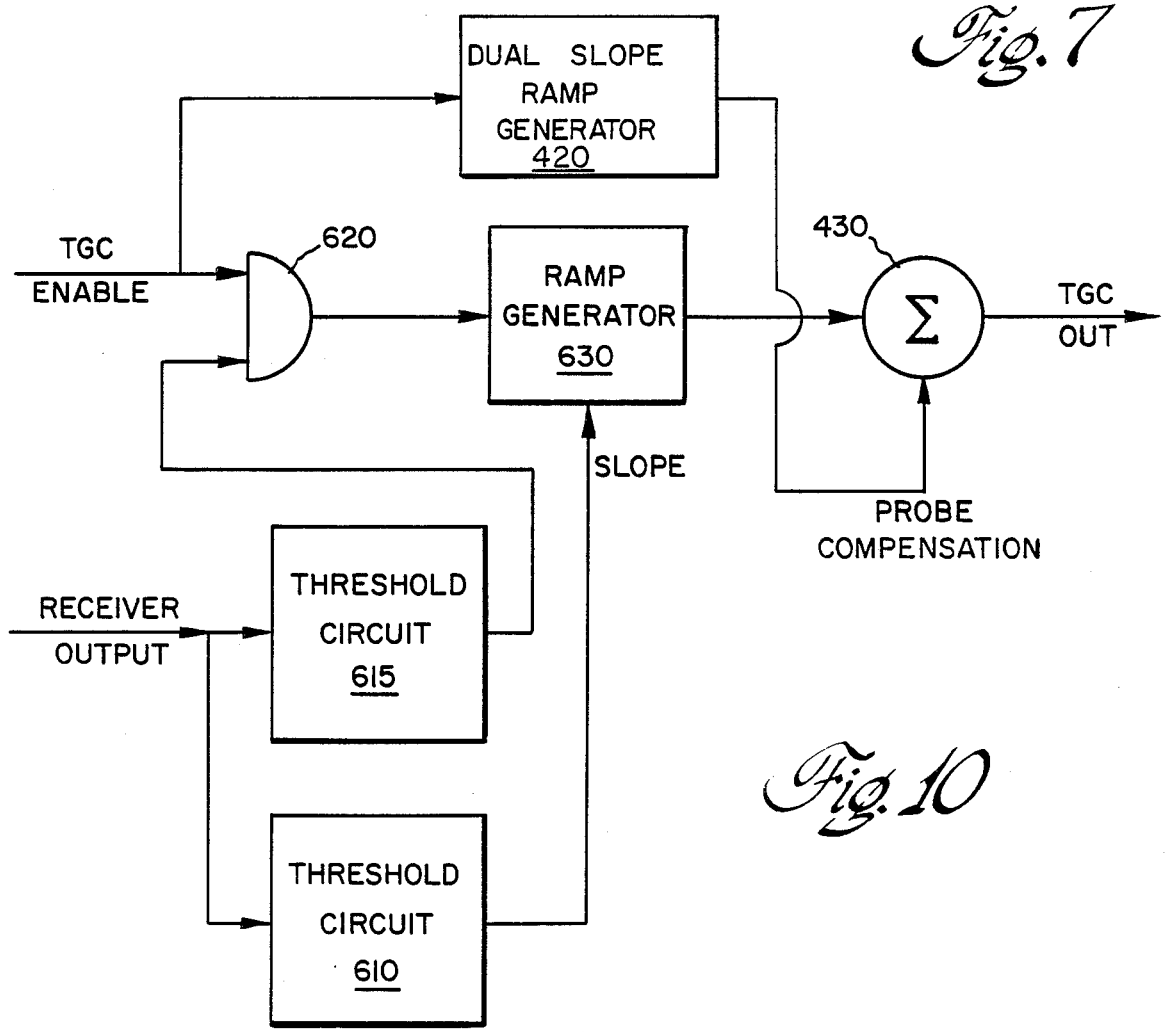
FIG. 10 is a circuit which utilizes signature information in ultrasound echos to adjust a time-gain compensation curve.

FIG. 10 is a circuit for implementing the foregoing method. The output of the receiver is applied to a threshold circuit 610 which compares the average scatter echo return level with the first threshold level 600. The output of the threshold circuit 610 controls the slope of the ramp generator 630 to provide a ramp signal having a large slope whenever the threshold is exceeded and a small slope whenever the threshold is not exceeded. A second threshold circuit 615 compares the scatter level with the second threshold level. A gate 620 is driven by the output of the second threshold circuit 615 and controls the ramp generator to stop the ramp run-up during those periods when the scatter return level is less than the second threshold level. The output of the ramp generator is summed with the probe compensation signal and applied to the receiver TGC input in the same manner as the signals of FIG. 7.

The methods and apparatus of the invention may, thus, be used to control the slope of the time-gain compensation in an echo ultrasound receiver to accurately match the attenuation characteristics of various tissue types and to improve the diagnostic quality of the information furnished by the system.

What is claimed is:

1. A method for processing received signals in an echo ultrasound examination system comprising the steps of:
   amplifying the signals with a gain controlled amplifier;
   increasing the gain of the amplifier as a function of time to compensate for the attenuation of ultrasound energy at varying depths within a body;
   identifying characteristic signatures of varying tissue types by measuring the level of scattered echos returned from said tissue types; and
   adjusting the rate of the gain variation of the amplifier, in response to said signatures, to compensate for the varying degrees of attenuation attributable to different tissue types.

2. The method of claim 1 wherein highly attenuating tissues are identified with high levels of scattered energy and less attenuating tissues are identified with lower levels of scattered energy.

3. The method of claim 2 wherein the level of scattered energy is determined by comparing the level of scattered echo signals with a predetermined threshold.

4. The method of claims 1, 2, or 3 further comprising the step of adjusting the gain of the amplifier to compensate for focussing effects in a transducer probe.

5. The method of claim 4 wherein the amplifier has a time-gain transfer function which is linear within plus or minus 1 dB over the dynamic working range of the receiver.

6. Apparatus for compensation of an echo ultrasound examination system comprising:
   a gain controlled amplifier connected to amplify echo signals received from a body;
   a time-gain compensation ramp generator connected to control the gain of the amplifier receiver; and
   means for identifying signal signatures characteristic of body tissue types having varying attenuation levels in scattered echo signals returned from said tissue types and for controlling the slope of a time-gain compensation ramp produced by said generator in response to the identification.

7. The apparatus of claim 6 wherein the means for identifying comprise one or more threshold circuits.

8. The apparatus of claim 6 wherein the means for identifying identify body wall tissue whenever the level of scattered echo signals exceeds a predetermined first threshold level.

9. The apparatus of claim 7 or 8 wherein the means for identifying identify tissue having low attenuation levels whenever the level of scattered echo signals does not exceed a second threshold level.

10. The apparatus of claim 6 further comprising means which vary the gain of the amplifier to compensate for focussing effects in a transducer probe.

11. The apparatus of claim 6 or 10 wherein the time-gain transfer function of the amplifier is linear to within plus or minus 1 dB over the working range of the receiver.

* * * * *